United States Patent
Kato et al.

(10) Patent No.: US 10,544,281 B2
(45) Date of Patent: Jan. 28, 2020

(54) ADDITION-CURABLE SILICONE RUBBER COMPOSITION AND CURED PRODUCT

(71) Applicant: SHIN-ETSU CHEMICAL CO., LTD., Tokyo (JP)

(72) Inventors: Nobu Kato, Annaka (JP); Munenao Hirokami, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 272 days.

(21) Appl. No.: 15/570,204

(22) PCT Filed: Jun. 7, 2016

(86) PCT No.: PCT/JP2016/066836
§ 371 (c)(1),
(2) Date: Oct. 27, 2017

(87) PCT Pub. No.: WO2016/199742
PCT Pub. Date: Dec. 15, 2016

(65) Prior Publication Data
US 2018/0134871 A1    May 17, 2018

(30) Foreign Application Priority Data
Jun. 9, 2015  (JP) .................. 2015-116724

(51) Int. Cl.
 *C08K 5/3475* (2006.01)
 *C07D 249/18* (2006.01)
 *C08L 83/04* (2006.01)

(52) U.S. Cl.
 CPC .......... *C08K 5/3475* (2013.01); *C07D 249/18* (2013.01); *C08L 83/04* (2013.01)

(58) Field of Classification Search
 CPC .................... C07D 249/18; C08L 3/04
 USPC ......................................... 524/91
 See application file for complete search history.

(56) References Cited

U.S. PATENT DOCUMENTS

| | | |
|---|---|---|
| 5,104,919 A | 4/1992 | Okami et al. |
| 5,936,054 A | 8/1999 | Achenbach et al. |
| 2003/0232202 A1 | 12/2003 | Yaginuma et al. |
| 2014/0179863 A1 | 6/2014 | Kato |

FOREIGN PATENT DOCUMENTS

| | | |
|---|---|---|
| JP | 2-242854 A | 9/1990 |
| JP | 10-077412 A | 3/1998 |
| JP | 2004-018701 A | 1/2004 |
| JP | 2014-156577 A | 8/2014 |
| JP | 104562039 A | 4/2015 |
| WO | WO 2004/046233 A1 | 6/2004 |

OTHER PUBLICATIONS

Extended European Search Report dated Nov. 26, 2018, in European Patent Application No. 16807449.0.
International Search Report (PCT/ISA/210) issued in PCT/JP2016/066836, dated Sep. 13, 2016.
Written Opinion (PCT/ISA/237) issued in PCT/JP2016/066836, dated Sep. 13. 2016.

*Primary Examiner* — Peter D. Mulcahy
(74) *Attorney, Agent, or Firm* — Birch, Stewart, Kolasch & Birch, LLP

(57) ABSTRACT

Provided is an addition-curable silicone rubber composition containing
 (A) an alkenyl group-containing organopolysiloxane having alkenyl groups bonded to at least two silicon atoms per molecule,
 (B) an organohydrogenpolysiloxane containing hydrogen atoms bonded to at least two silicon atoms per molecule,
 (C) a platinum catalyst, and
 (D) a benzotriazole derivative represented by general formula (I)

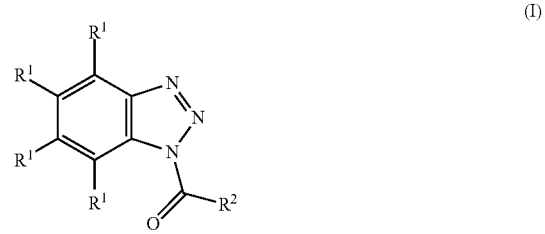

(in the formula, $R^1$ is a hydrogen atom or monovalent hydrocarbon group, $R^2$ is a monovalent organic group) that makes it possible to provide silicone rubber that can lower the compression set without harming the curing rate and suppress discoloration after a heat resistance test.

6 Claims, No Drawings

ADDITION-CURABLE SILICONE RUBBER COMPOSITION AND CURED PRODUCT

TECHNICAL FIELD

This invention relates to an addition-curable silicone rubber composition which cures into a silicone rubber or cured product having a low compression set and heat discoloration resistance without compromising mechanical properties (rubber properties) of silicone rubber and cure rate, and a cured product thereof.

BACKGROUND ART

Silicone rubbers are used in a wide variety of fields, for example, health care materials such as bottle teats and food-safe goods, hoses and gasket materials for automobile use, building members, and fiber coating materials because of heat resistance, freeze resistance, safety, appearance (transparency), touch, and durability.

Silicone rubbers used as O-rings and gaskets are required to have a low compression set for preventing seal leakage. Typical silicone rubbers, however, have a substantial compression set and suffer from the problem of rubber shape change during long-term service in high-temperature applications. In order to reduce the compression set, often the rubbers shaped by heat curing must be further subject to secondary vulcanization at high temperature for a long time.

To solve the problem, Patent Document 1: JP-A H02-242854 proposes to add a triazole compound to an addition-curable silicone rubber composition for reducing the compression set thereof without a need for secondary vulcanization. However, the addition of a triazole compound to the silicone rubber composition gives rise to the problem that the cure rate is decelerated.

PRIOR ART DOCUMENT

Patent Document

Patent Document 1: JP-A H02-242854

SUMMARY OF THE INVENTION

Problems to be Solved by the Invention

An object of the invention, which has been made to ameliorate the above-mentioned circumstances, is to provide an addition-curable silicone rubber composition in which a benzotriazole derivative of specific structure is added to reduce the compression set of a cured product thereof without decelerating the cure rate, and a cured product thereof.

Means for Solving the Problems

Making extensive investigations to attain the above object, the inventors have found that when a specific amount of a benzotriazole derivative of specific structure represented by the general formula (I) to be described below is added to an addition-curable silicone rubber composition comprising an organopolysiloxane containing silicon-bonded alkenyl, an organohydrogenpolysiloxane, and a platinum catalyst, there is obtained an addition-curable silicone rubber composition which cures into a silicone rubber or cured product having a low compression set without compromising the cure rate. The invention is predicated on this finding.

Accordingly, the invention provides an addition-curable silicone rubber composition and a cured product thereof as defined below.

[1] An addition-curable silicone rubber composition comprising:
(A) 100 parts by weight of an alkenyl-containing organopolysiloxane having at least two silicon-bonded alkenyl groups per molecule,
(B) an organohydrogenpolysiloxane having at least two silicon-bonded hydrogen atoms per molecule, in an amount of 0.2 to 20 parts by weight per 100 parts by weight of component (A),
(C) a catalytic amount of a platinum catalyst, and
(D) a benzotriazole derivative having the general formula (I):

[Chemical Formula 1]

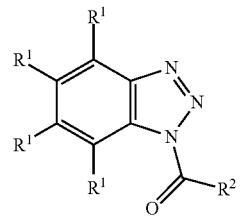

wherein $R^1$ is hydrogen or a $C_1$-$C_{10}$ monovalent hydrocarbon group and $R^2$ is a monovalent organic group, in an amount of 2 to 1,000 moles per mole of platinum atom in component (C).

[2] The silicone rubber composition of [1] wherein in formula (I), $R^2$ is a $C_1$-$C_{10}$ monovalent hydrocarbon group or a group having the following formula:

[Chemical Formula 2]

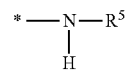

wherein $R^5$ is a $C_1$-$C_{15}$ monovalent hydrocarbon group or —$(CH_2)_p$—$Si(OR^6)_3$ wherein $R^6$ is a $C_1$-$C_4$ alkyl group or $SiR^7_3$ group (wherein $R^7$ is $C_1$-$C_4$ alkyl) and p is an integer of 1 to 6, and * designates a bonding site.

[3] The silicone rubber composition of [1] or [2], further comprising (E) 1 to 100 parts by weight per 100 parts by weight of component (A) of a reinforcing filler.

[4] The silicone rubber composition of [3] wherein component (E) is fumed silica having a specific surface area of at least 50 $m^2$/g as measured by the BET method.

[5] The silicone rubber composition of any one of [1] to [4] wherein provided that T10 is a 10% cure time and T90 is a 90% cure time during measurement at 130° C. for 2 minutes, a value of T90-T10 is up to 40 seconds.

[6] A cured silicone rubber which is formed by curing the silicone rubber composition of any one of [1] to [5] and has a compression set of up to 30% after compressed 25% at 150° C. for 22 hours.

Advantageous Effects of the Invention

The addition-curable silicone rubber composition of the invention comprising components (A) to (D) blended in specific amounts affords a silicone rubber having a low compression set without compromising the cure rate. The resulting silicone rubber experiences minimal discoloration after a heat resistance test.

EMBODIMENT FOR CARRYING OUT THE INVENTION

Now the invention is described in detail.

Component (A), which is a main component (i.e., base polymer) of the composition, is an organopolysiloxane having at least two silicon-bonded alkenyl groups per molecule. Specifically, the organopolysiloxane has a structure of the average compositional formula (II).

$$R^3{}_a SiO_{(4-a)/2} \tag{II}$$

Herein $R^3$ which may be the same or different is a substituted or unsubstituted monovalent hydrocarbon group of 1 to 15 carbon atoms, preferably 1 to 10 carbon atoms, and more preferably 1 to 8 carbon atoms, a is a positive number of 1.5 to 2.8, preferably 1.8 to 2.5, and more preferably 1.95 to 2.05.

Examples of the silicon-bonded substituted or unsubstituted monovalent hydrocarbon group of 1 to 15 carbon atoms, preferably 1 to 10 carbon atoms, and more preferably 1 to 8 carbon atoms, represented by $R^3$ include alkyl groups such as methyl, ethyl, propyl, isopropyl, butyl, isobutyl, tert-butyl, pentyl, neopentyl, hexyl, cyclohexyl, octyl, nonyl, and decyl; aryl groups such as phenyl, tolyl, xylyl, and naphthyl; aralkyl groups such as benzyl, phenylethyl, and phenylpropyl; alkenyl groups such as vinyl, allyl, propenyl, isopropenyl, butenyl, hexenyl, cyclohexenyl, and octenyl; and substituted forms of the foregoing groups in which some or all hydrogen atoms are substituted by halogen atoms (e.g., fluorine, bromine and chlorine), cyano or the like, such as chloromethyl, chloropropyl, bromoethyl, trifluoropropyl, and cyanoethyl. It is preferred that at least 90 mol % of $R^3$ groups be methyl.

Of $R^3$ groups, at least two groups must be alkenyl groups, preferably of 2 to 8 carbon atoms, more preferably of 2 to 6 carbon atoms, and most preferably vinyl.

In the organopolysiloxane, the content of alkenyl groups is preferably $1.0 \times 10^{-6}$ mol/g to $3.0 \times 10^{-3}$ mol/g, more preferably $1.0 \times 10^{-5}$ mol/g to $2.0 \times 10^{-3}$ mol/g. An organopolysiloxane containing less than $1.0 \times 10^{-6}$ mol/g of alkenyl may have too low a rubber hardness and become gel. An alkenyl content in excess of $3.0 \times 10^{-3}$ mol/g may give an extremely high crosslinking density, resulting in rubber having an extremely high hardness and devoid of elasticity. The alkenyl group may be bonded to the silicon atom at the end of the molecular chain and/or a silicon atom midway the molecular chain (i.e., at a non-terminal position of the molecular chain).

The organopolysiloxane is preferably a linear diorganopolysiloxane capped at either end of the molecular chain with a triorganosiloxy group ($R^3{}_3SiO_{1/2}$) and having a backbone composed of repeating diorganosiloxane units ($R^3{}_2SiO_{2/2}$). An organopolysiloxane partially containing a branched or cyclic structure having monoorganosilsesquioxane units ($R^3SiO_{3/2}$) is also acceptable. Herein $R^3$ is as defined above.

With respect to molecular weight or degree of polymerization, the organopolysiloxane typically has an average degree of polymerization (i.e., number average degree of polymerization, the same applies hereinafter) of 100 to 50,000, preferably 150 to 20,000. An organopolysiloxane having a degree of polymerization of less than 100 may fail to provide a cured product with adequate rubber texture whereas an organopolysiloxane having a degree of polymerization in excess of 50,000 may have too high a viscosity to mold. The molecular weight or degree of polymerization may be measured, for example, as number average molecular weight or number average degree of polymerization by gel permeation chromatography (GPC) versus polystyrene standards using toluene as developing solvent (the same applies hereinafter).

Examples of the organopolysiloxane as component (A) include
molecular both end diorganoalkenylsiloxy-blocked diorganopolysiloxane,
molecular both end organodialkenylsiloxy-blocked diorganopolysiloxane,
molecular both end trialkenylsiloxy-blocked diorganopolysiloxane,
molecular both end triorganosiloxy-blocked diorganosiloxane/organoalkenylsiloxane copolymers,
molecular both end diorganoalkenylsiloxy-blocked diorganosiloxane/organoalkenylsiloxane copolymers, and
diorganosiloxane/organoalkenylsiloxane copolymers blocked at one end with a diorganoalkenylsiloxy group and at the other end with a triorganosiloxy group.
Inter alia, molecular both end diorganoalkenylsiloxy-blocked diorganopolysiloxane, molecular both end triorganosiloxy-blocked diorganosiloxane/organoalkenylsiloxane copolymers, and molecular both end diorganoalkenylsiloxy-blocked diorganosiloxane/organoalkenylsiloxane copolymers are preferred. The "organo" group in each siloxane means a substituted or unsubstituted monovalent hydrocarbon group (exclusive of aliphatic unsaturated groups such as alkenyl) as exemplified for $R^3$ in formula (II).

Component (B) is an organohydrogenpolysiloxane having at least 2, preferably at least 3 silicon-bonded hydrogen atoms (or SiH groups) in a molecule. Component (B) serves as a curing agent or crosslinker for curing the composition through the mechanism that hydrosilylation or addition reaction takes place between SiH groups in its molecule and silicon-bonded alkenyl groups in component (A) to form crosslinks.

Preferred as component (B) is an organohydrogenpolysiloxane having at least 2, preferably at least 3, more preferably 3 to 100, and most preferably 4 to 50 silicon-bonded hydrogen atoms (or SiH groups) in a molecule, represented by the average compositional formula (III).

$$R^4{}_b H_c SiO_{(4-b-c)/2} \tag{III}$$

Herein $R^4$ which may be the same or different is a substituted or unsubstituted monovalent hydrocarbon group of 1 to 15 carbon atoms, preferably 1 to 10 carbon atoms, and more preferably 1 to 8 carbon atoms, b is a positive number of 0.7 to 2.1, c is a positive number of 0.001 to 0.1, and b+c is 0.8 to 3.0.

Examples of the monovalent hydrocarbon group represented by $R^4$ are as exemplified above for $R^3$, with hydrocarbon groups free of aliphatic unsaturation being preferred.

The subscript b is a positive number of 0.7 to 2.1, preferably 0.8 to 2.0, c is a positive number of 0.001 to 1.0, preferably 0.01 to 1.0, and the sum of b+c is 0.8 to 3.0, preferably 1.0 to 2.5. The molecular structure of the organohydrogenpolysiloxane may be linear, cyclic, branched or three-dimensional network.

In the organohydrogenpolysiloxane, the content of SiH groups is preferably 0.0005 mol/g to 0.020 mol/g, more preferably 0.001 mol/g to 0.017 mol/g. A SiH content of less than 0.0005 mol/g may lead to insufficient crosslinking whereas an organohydrogenpolysiloxane with a SiH content in excess of 0.020 mol/g may be unstable.

More preferred is an organohydrogenpolysiloxane in which the number of silicon atoms per molecule (i.e., degree of polymerization) is about 2 to about 300, even more preferably about 3 to about 150, most preferably about 4 to about 100 and which is liquid at room temperature (25° C.). The silicon-bonded hydrogen atom may be present at the end of the molecular chain and/or at a position midway the molecular chain (i.e., at a non-terminal position).

Examples of the organohydrogenpolysiloxane as component (B) include
1,1,3,3-tetramethyldisiloxane, 1,3,5,7-tetramethylcyclotetrasiloxane,
tris(hydrogendimethylsiloxy)methylsilane, tris(hydrogendimethylsiloxy)phenylsilane,
methylhydrogencyclopolysiloxane,
methylhydrogensiloxane/dimethylsiloxane cyclic copolymers,
molecular both end trimethylsiloxy-blocked methylhydrogenpolysiloxane,
molecular both end trimethylsiloxy-blocked dimethylsiloxane/methylhydrogensiloxane copolymers,
molecular both end dimethylhydrogensiloxy-blocked dimethylpolysiloxane.
molecular both end dimethylhydrogensiloxy-blocked dimethylsiloxane/methylhydrogensiloxane copolymers,
molecular both end trimethylsiloxy-blocked methylhydrogensiloxane/diphenylsiloxane copolymers,
molecular both end trimethylsiloxy-blocked methylhydrogensiloxane/diphenylsiloxane/dimethylsiloxane copolymers,
molecular both end trimethylsiloxy-blocked methylhydrogensiloxane/methylphenylsiloxane/dimethylsiloxane copolymers,
molecular both end dimethylhydrogensiloxy-blocked methylhydrogensiloxane/dimethylsiloxane/diphenylsiloxane copolymers,
molecular both end dimethylhydrogensiloxy-blocked methylhydrogensiloxane/dimethylsiloxane/methylphenylsiloxane copolymers,
copolymers consisting of $(CH_3)_2HSiO_{1/2}$ units, $(CH_3)_3SiO_{1/2}$ units and $SiO_{4/2}$ units,
copolymers consisting of $(CH_3)_2HSiO_{1/2}$ units and $SiO_{4/2}$ units,
copolymers consisting of $(CH_3)_2HSiO_{1/2}$ units, $SiO_{4/2}$ units and $(C_6H_5)SiO_{3/2}$ units, and
other forms of the foregoing in which some or all methyl groups are substituted by other alkyl groups or phenyl groups.

The organohydrogenpolysiloxane (B) may also be a polyvalent aromatic ring-containing organohydrogenpolysiloxane which corresponds to the above-exemplified compound or similar compound, but has a di- to tetravalent aromatic ring-containing hydrocarbon skeleton (e.g., phenylene skeleton, bisphenylene skeleton, bis(phenylene)ether skeleton, bis(phenylene)methane skeleton, 2,2-bis(phenylene)propane skeleton, and 2,2-bis(phenylene)hexafluoropropane skeleton) in some of siloxane skeletons (—Si—O—Si—) (typically, at some of the positions of oxygen atoms in siloxane bonds) to constitute its molecule.

The organohydrogenpolysiloxane (B) is added in an amount of 0.2 to 20 parts, preferably 0.3 to 10 parts by weight per 100 parts by weight of component (A). Component (B) is preferably added in such an amount that the molar ratio of silicon-bonded hydrogens (or SiH) in organohydrogenpolysiloxane (B) to total silicon-bonded alkenyl groups in components (A) and (B), especially component (A), referred to as "SiH/alkenyl ratio", may be from 0.8/1 to 10/1, more preferably 1.0/1 to 5/1. If the SiH/alkenyl ratio is less than 0.8, cure or crosslinking density may be insufficient, resulting in a sticky rubber. If the SiH/alkenyl ratio exceeds 10, a molded silicone rubber may contain bubbles or its mold release be difficult.

Component (C) is a platinum catalyst, examples of which are platinum group metal base catalysts including platinum black, platinic chloride, chloroplatinic acid, the reaction product of chloroplatinic acid with monohydric alcohol, chloroplatinic acid-olefin complexes, and platinum bisacetoacetate.

The platinum catalyst may be used in a catalytic amount, which is typically about 0.5 to about 1,000 ppm, specifically about 1 to about 500 ppm of platinum group metal based on the total weight of components (A) to (D), or components (A) to (E) when component (E) to be described below is blended.

Component (D) is a benzotriazole derivative having the general formula (I):

[Chemical Formula 3]

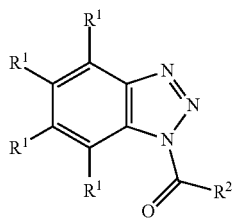

(I)

wherein $R^1$ is hydrogen or a monovalent hydrocarbon group of 1 to 10 carbon atoms, specifically 1 to 6 carbon atoms and $R^2$ is a monovalent organic group. The benzotriazole derivative interacts with the platinum catalyst as component (C) so as to reduce the compression set of a cured silicone rubber.

Herein $R^1$ is hydrogen or a monovalent hydrocarbon group of 1 to 10 carbon atoms, preferably 1 to 6 carbon atoms. Examples of the $C_1$-$C_6$ monovalent hydrocarbon group include alkyl groups such as methyl, ethyl, propyl, isopropyl, butyl, isobutyl, tert-butyl, pentyl, neopentyl, hexyl, and cyclohexyl; and substituted forms of the foregoing groups in which some or all hydrogen atoms are substituted by halogen atoms (e.g., fluorine, bromine and chlorine), cyano or the like, such as chloromethyl, chloropropyl, bromoethyl, trifluoropropyl, and cyanoethyl. Of these, hydrogen and methyl are preferred in view of synthesis.

$R^2$ is a monovalent organic group, examples include $C_1$-$C_{10}$ monovalent hydrocarbon groups, for example, alkyl groups such as methyl, ethyl, propyl, isopropyl, butyl, isobutyl, tert-butyl, pentyl, neopentyl, hexyl, and cyclohexyl aryl groups such as phenyl, tolyl, xylyl, and naphthyl; aralkyl groups such as benzyl, phenylethyl, and phenylpropyl; and groups having the following formula.

[Chemical Formula 4]

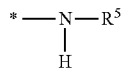

Herein $R^5$ is a monovalent hydrocarbon group, typically alkyl, of 1 to 15 carbon atoms, specifically 1 to 10 carbon atoms, or —$(CH_2)_p$—$Si(OR^6)_3$ wherein $R^6$ is an alkyl group of 1 to 4 carbon atoms, specifically 1 to 3 carbon atoms or $SiR^7_3$ group wherein $R^7$ is an alkyl group of 1 to 4 carbon atoms, specifically 1 to 3 carbon atoms, p is an integer of 1 to 6, specifically 1 to 3, and * designates a bonding site.

Examples of benzotriazole derivative are given below.

[Chemical Formula 5]

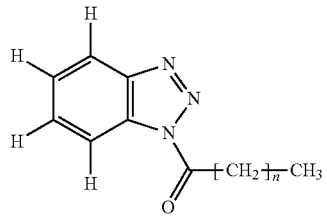

Herein n is an integer of 0 to 6.

[Chemical Formula 6]

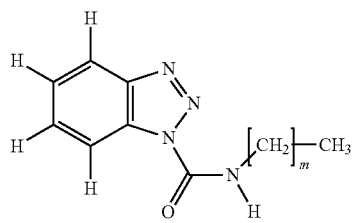

Herein m is an integer of 1 to 6.

[Chemical Formula 7]

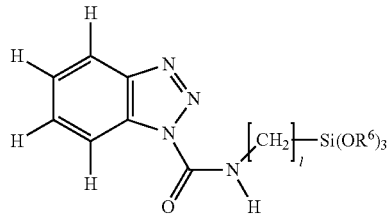

Herein 1 is an integer of 1 to 6 and $R^6$ is alkyl or trialkylsilyl.

Of these, most preferred groups are given by the following formulae.

[Chemical Formula 8]

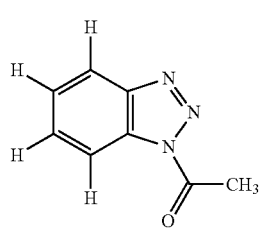

[Chemical Formula 9]

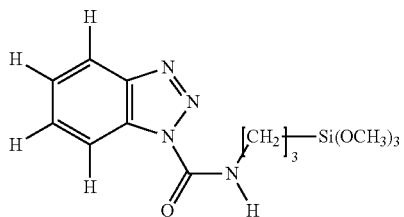

[Chemical Formula 10]

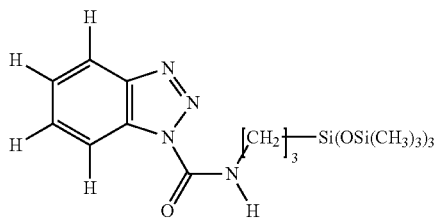

[Chemical Formula 11]

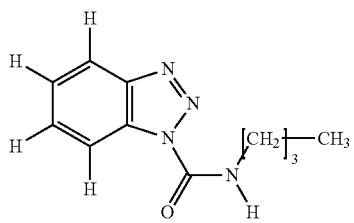

The amount of component (D) blended is 2 to 1,000 moles, preferably 2 to 800 moles, more preferably 2 to 500 moles, and even more preferably 2 to 100 moles per mole of platinum atom in component (C). Less than 2 moles of component (D) is too small to reduce a compression set sufficiently whereas more than 1,000 moles of component (D) may interfere with cure.

To the silicone rubber composition, a reinforcing filler is preferably added as component (E). In this embodiment, the reinforcing filler is preferably reinforcing silica fine powder, which may be any type of silica commonly used as rubber reinforcement. Although any silica fine powder used in conventional silicone rubber compositions is useful, the reinforcing silica fine powder should preferably have a specific surface area of at least 50 m²/g as measured by the BET method. It is advantageous to use precipitated silica (wet silica), fumed silica (dry silica) and fired silica having a BET specific surface area of 50 to 400 m²/g, specifically 100 to 350 m²/g, with the fumed silica being especially advantageous for improved rubber strength. The reinforcing silica fine powder may be surface treated with organosilicon compounds, typically hydrolyzable organosilicon compounds such as chlorosilanes, alkoxysilanes and organosilazanes for rendering the surface hydrophobic. The silica powder may be directly surface treated (to be hydrophobic) in the powder state with a surface treating agent prior to use. Alternatively, the silica powder may be surface treated (to be hydrophobic) by adding a surface treating agent during the step of mixing the silica powder with silicone oil (e.g., alkenyl-containing organopolysiloxane (A)).

For the surface treatment, any well-known techniques may be used. For example, an untreated silica fine powder and a surface treating agent are admitted into a mechanical milling device closed under atmospheric pressure or a fluidized bed where they are mixed to effect surface treatment at room temperature (or elevated temperature), optionally in the presence of an inert gas. If desired, a catalyst (e.g., hydrolysis accelerant) is used to promote the surface treatment. The mixing step is followed by drying, yielding a treated silica fine powder. The amount of the surface treating agent used may be at least the theoretical amount calculated from the surface area of powder to be covered with the agent.

Suitable treating agents include silazanes such as hexamethyldisilazane; silane coupling agents such as methyltrimethoxysilane, ethyltrimethoxysilane, propyltrimethoxysilane, butyltrimethoxysilane, dimethyldimethoxysilane, diethyldimethoxysilane, vinyltriethoxysilane, vinyltrimethoxysilane, trimethylmethoxysilane, triethylmethoxysilane, vinyltris(methoxyethoxy)silane, trimethylchlorosilane, dimethyldichlorosilane, divinyldimethoxysilane and chloropropyltrimethoxysilane; and organosilicon compounds such as polymethylsiloxane and organohydrogenpolysiloxane. After the surface treatment with such agents, the resulting silica fine particles are hydrophobic and ready for use. Of these treating agents, the silane coupling agents and silazanes are preferred.

The amount of component (E) blended is 1 to 100 parts, preferably 5 to 60 parts, and more preferably 10 to 60 parts by weight per 100 parts by weight of component (A). Less than 1 part by weight of component (E) is insufficient for reinforcement whereas a silicone rubber composition with more than 100 parts by weight of component (E) is too viscous to work or process.

Other components may be compounded in the addition-curable silicone rubber composition, if necessary. Included are fillers such as quartz powder, diatomaceous earth, and calcium carbonate; conductive agents such as carbon black, conductive zinc oxide, and metal powder; hydrosilylation inhibitors such as nitrogen-containing compounds, acetylene compounds, phosphorus compounds, nitrile compounds, carboxylates, tin compounds, mercury compounds, and sulfur compounds; heat resistance enhancers such as iron oxide and cerium oxide; internal mold release agents such as dimethylsilicone oil; adhesion promoters such as organosilicon compounds, typically alkoxysilanes, containing at least one functional group selected from alkenyl, epoxy, amino, (meth)acryloxy, and mercapto groups, but not SiH groups in the molecule; and thixotropic agents.

The addition-curable silicone rubber composition may be molded and cured in accordance with standard methods. An appropriate molding method may be selected from injection molding, transfer molding, cast molding, and compression molding depending on the intended application. For curing, heat treatment (or primary vulcanization) may be carried out at 40 to 230° C. for about 3 seconds to about 160 minutes. Optionally, the cured composition may be post-cured (or secondary vulcanization) at 40 to 230° C. for about 10 minutes to about 24 hours.

The cure speed of the addition-curable silicone rubber composition is defined by computing a value of T90-T10 using T10 (in sec) which is a 10% cure time (i.e., a time taken from the start of measurement until the torque value reaches 10% of the maximum torque value at 2 minutes from the start of measurement, at 130° C.) and T90 (in sec) which is a 90% cure time (i.e., a time taken from the start of measurement until the torque value reaches 90% of the maximum torque value at 2 minutes from the start of measurement, at 130° C.) as measured at 130° C. for 2 minutes by a cure tester (e.g., rotorless disc rheometer or moving die rheometer (MDR)). With a focus on molding efficiency, the value of T90-T10 is preferably up to 40 seconds, more preferably up to 30 seconds. A value of T90-T10 in excess of 40 seconds indicates a redundant molding cycle which may be uneconomical.

The addition-curable silicone rubber composition is cured into a cured product (silicone rubber) having a compression set of up to 30%, specifically up to 20%, and more specifically up to 15% by compression set measurement under conditions: 25% compression at 150° C. for 22 hours, according to JIS-K6249. The silicone rubbers having a compression set of up to 30% are preferred as the material for O-rings and gaskets. The addition-curable silicone rubber composition having a compression set in the range is obtained by blending component (D) in a specific ratio with a conventional addition-curable silicone rubber composition containing components (A) to (C) until uniform.

The addition-curable silicone rubber composition is useful in the application where a compression set as low as possible is required, especially as seal materials such as O-rings and gaskets.

EXAMPLE

Examples and Comparative Examples of the invention are given below by way of illustration and not by way of limitation. All parts are by weight. The average degree of polymerization is a number average degree of polymerization as measured by gel permeation chromatography (GPC) versus polystyrene standards using toluene as developing solvent.

Example 1

Molecular both end dimethylvinylsiloxy-blocked dimethylpolysiloxane (A1) having an average degree of polymerization of 750, 100 parts, was mixed with 1.30 parts (SiH/vinyl=2.0 mol/mol) of methylhydrogenpolysiloxane (B1) blocked at molecular both ends with trimethylsiloxy, having SiH groups on side chains (molecular both end trimethylsiloxy-blocked dimethylsiloxane/methylhydrogensiloxane copolymer having a degree of polymerization of 80 and a SiH content of 0.0055 mol/g) as a crosslinker, and 0.05 part of ethynylcyclohexanol as a reaction inhibitor at room temperature for 15 minutes. Then, 0.10 part of a toluene solution of platinum-1,3-divinyl-1,1,3,3-tetramethyldisiloxane complex (C1) having a Pt concentration of 1 wt % was added to the mixture, which was stirred at room temperature for 15 minutes, yielding a silicone rubber blend A.

To 100 parts of the silicone rubber blend A, 0.007 part (benzotriazole derivative/Pt atom=8.5 mol/mol) of a benzotriazole derivative (D1) having the following formula was added to form a uniform silicone rubber composition.

[Chemical Formula 12]

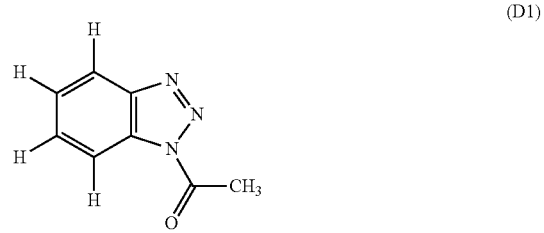

(D1)

The composition was measured for cure at 130° C. by a rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C., test duration 22 hours) according to JIS-K6249, and visually observed for outer appearance (i.e., color) of the sample after the compression set test. The results are shown in Table 1.

Example 2

To 100 parts of the silicone rubber blend A in Example 1, 0.009 part (benzotriazole derivative/Pt atom=8.0 mol/mol) of a benzotriazole derivative (D2) having the following formula was added to form a uniform silicone rubber composition.

[Chemical Formula 13]

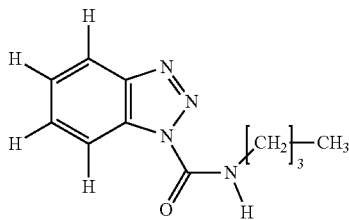

(D2)

The composition was measured for cure at 130° C. by rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C. test duration 22 hours) according to JIS-K6249, and visually observed for outer appearance (i.e., color) of the sample after the compression set test. The results are shown in Table 1.

Example 3

To 100 parts of the silicone rubber blend A in Example 1, 0.0135 part (benzotriazole derivative/Pt atom=8.2 mol/mol) of a benzotriazole derivative (D3) having the following formula was added to form a uniform silicone rubber composition.

[Chemical Formula 14]

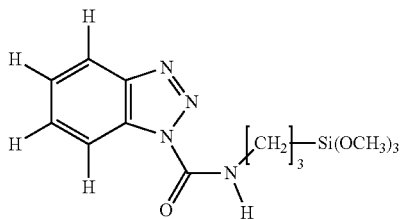

(D3)

The composition was measured for cure at 130° C. by rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C. test duration 22 hours) according to JIS-K6249, and visually observed for outer appearance (i.e., color) of the sample after the compression set test. The results are shown in Table 1.

Example 4

To 100 parts of the silicone rubber blend A in Example 1, 0.0225 part (benzotriazole derivative/Pt atom=8.8 mol/mol) of a benzotriazole derivative (D4) having the following formula was added to form a uniform silicone rubber composition.

[Chemical Formula 15]

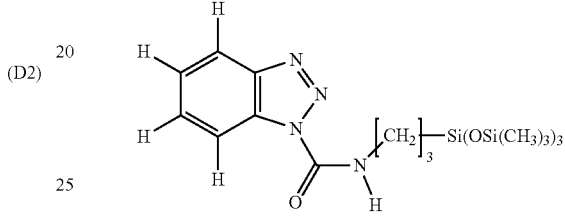

(D4)

The composition was measured for cure at 130° C. by rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C., test duration 22 hours) according to JIS-K6249, and visually observed for outer appearance (i.e., color) of the sample after the compression set test. The results are shown in Table 1.

Comparative Example 1

The silicone rubber blend A in Example 1 prior to addition of a benzotriazole derivative was measured for cure at 130° C. by rheometer MDR2000 (Alpha Technologies), with the results shown in Table 1. Also the silicone rubber blend A was press cured at 120° C. for 15 minutes to form a cured product. The cured product was visually observed for outer appearance (i.e., color), measured for compression set (compression 25%, temperature 150° C., test duration 22 hours) according to JIS-K6249, and visually observed for outer appearance (i.e., color) of the sample after the compression set test. The results are shown in Table 1.

Comparative Example 2

To 100 parts of the silicone rubber blend A in Example 1, 0.005 part (benzotriazole/Pt atom=8.2 mol/mol) of benzotriazole was added to form a uniform silicone rubber composition. The composition was measured for cure at 130° C. by rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C. test duration 22 hours) according to JIS-K6249, and visually observed for outer appearance (i.e., color) of the sample after the compression set test. The results are shown in Table 1.

Comparative Example 3

To 100 parts of the silicone rubber blend A in Example 1, 0.0055 part (benzotriazole derivative/Pt atom=8.0 mol/mol) of a benzotriazole derivative (D5) having the following formula was added to form a uniform silicone rubber composition.

[Chemical Formula 16]

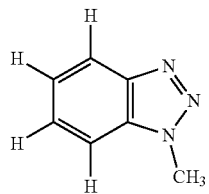

(D5)

The composition was measured for cure at 130° C. by rheometer MDR2000 (Alpha Technologies), with the results shown in Table 1. Also the composition was press cured at 120° C. for 15 minutes to form a cured product. The cured product was visually observed for outer appearance (i.e., color), measured for compression set (compression 25%, temperature 150° C. test duration 22 hours) according to JIS-K6249, and visually observed for outer appearance (i.e., color) of the sample after the compression set test. The results are shown in Table 1.

Example 5

Molecular both end dimethylvinylsiloxy-blocked dimethylpolysiloxane (A1) having an average degree of polymerization of 750, 60 parts, was mixed with 40 parts of fumed silica (E1) having a BET specific surface area of 300 m²/g (Aerosil 300, Nippon Aerosil Co., Ltd.), 8 parts of hexamethyldisilazane, and 2.0 parts of water at room temperature for 30 minutes. The mixture was heated at 150° C., stirred for 3 hours, and cooled, yielding a silicone rubber base.

To 100 parts of the silicone rubber base, were added 40 parts of the dimethylpolysiloxane (A1), 5 parts of dimethylpolysiloxane (A2) blocked at molecular both ends with trimethylsiloxy, having methyl groups on side chains (i.e., monovalent groups or atoms bonded to silicon atoms on diorganosiloxane units of the backbone, the same holds true hereinafter), 2.5 mol % of which are replaced by vinyl groups, and having an average degree of polymerization of 200, 1.79 parts (SiH/vinyl=1.8 mol/mol) of methylhydrogenpolysiloxane (B2) blocked at molecular both ends with trimethylsiloxy and having SiH groups on side chains (molecular both end trimethylsiloxy-blocked dimethylsiloxane/methylhydrogensiloxane copolymer having a degree of polymerization of 27 and a SiH content of 0.0069 mol/g) as a crosslinker, and 0.12 part of ethynylcyclohexanol as a reaction inhibitor. The mixture was stirred for 15 minutes. Then, 0.10 part of a toluene solution of platinum-1,3-divinyl-1,1,3,3-tetramethyldisiloxane complex (C1) having a Pt concentration of 1 wt % was added to the mixture, which was stirred for 30 minutes, yielding a uniform silicone rubber blend B.

To 100 parts of the silicone rubber blend B, 0.007 part (benzotriazole derivative/Pt atom=12.5 mol/mol) of benzotriazole derivative (D1) in Example 1 was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

Example 6

To 100 parts of the silicone rubber blend B in Example 5, 0.009 part (benzotriazole derivative/Pt atom=11.8 mol/mol) of benzotriazole derivative (D2) in Example 2 was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

Example 7

To 100 parts of the silicone rubber blend B in Example 5, 0.0135 part (benzotriazole derivative/Pt atom=11.9 mol/mol) of benzotriazole derivative (D3) in Example 3 was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

Example 8

To 100 parts of the silicone rubber blend B in Example 5, 0.0225 part (benzotriazole derivative/Pt atom=12.9 mol/mol) of benzotriazole derivative (D4) in Example 4 was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

Example 9

To 100 parts of the silicone rubber blend B in Example 5, 0.10 part (benzotriazole derivative/Pt atom=88 mol/mol) of benzotriazole derivative (D3) in Example 3 was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression: 25%, temperature: 150° C., test duration: 22 hours) according to JIS-K6249, and visually observed for outer appearance (i.e., color) of the sample after the compression set test. The results are shown in Table 2.

Comparative Example 4

The silicone rubber blend B in Example 5 prior to addition of a benzotriazole derivative was measured for cure at 130° C. by rheometer MDR2000 (Alpha Technologies), with the results shown in Table 2. Also the silicone rubber blend B was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

Comparative Example 5

To 100 parts of the silicone rubber blend B in Example 5, 0.005 part (benzotriazole/Pt atom=12.0 mol/mol) of benzotriazole was added to form a uniform silicone rubber composition. The composition was measured for cure at 130° C. by rheometer MDR2000 (Alpha Technologies), with the results shown in Table 2. Also the composition was press cured at 120° C. for 15 minutes to form a cured product. The cured product was visually observed for outer appearance (i.e., color), measured for a compression set (compression 25%, temperature 150° C., test duration 22 hours) according to JIS-K6249, and visually observed for outer appearance (i.e., color) of the sample after the compression set test. The results are shown in Table 2.

The invention claimed is:

1. An addition-curable silicone rubber composition comprising:

(A) 100 parts by weight of an alkenyl-containing organopolysiloxane having at least two silicon-bonded alkenyl groups per molecule, (B) an organohydrogenpolysiloxane having at least two silicon-bonded hydrogen atoms per molecule, in an amount of 0.2 to 20 parts by weight per 100 parts by weight of component (A), (C) a catalytic amount of a platinum catalyst, and (D) a benzotriazole derivative having the general formula (I):

[Chemical Formula 1]

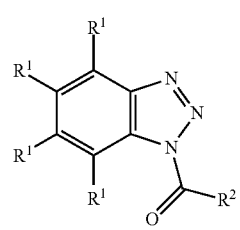

(I)

wherein $R^1$ is hydrogen or a $C_1$-$C_{10}$ monovalent hydrocarbon group and $R^2$ is a monovalent organic group, in an amount of 2 to 1,000 moles per mole of platinum atom in component (C).

2. The silicone rubber composition of claim 1 wherein in formula (I), $R^2$ is a $C_1$-$C_{10}$ monovalent hydrocarbon group or a group having the following formula:

TABLE 1

| | Example | | | | Comparative Example | | |
|---|---|---|---|---|---|---|---|
| | 1 | 2 | 3 | 4 | 1 | 2 | 3 |
| Cure time T10 (sec) | 25 | 28 | 26 | 23 | 25 | 29 | 29 |
| Cure time T90 (sec) | 54 | 59 | 55 | 44 | 46 | 95 | 60 |
| T90-T10 (sec) | 29 | 31 | 29 | 21 | 21 | 66 | 31 |
| Appearance or color | colorless | colorless | colorless | colorless | colorless | colorless | colorless |
| Compression set (%) | 14 | 5 | 7 | 13 | 53 | 29 | 43 |
| Appearance or color after the test | colorless | colorless | colorless | colorless | yellow | colorless | yellow |

TABLE 2

| | Example | | | | | Comparative Example | |
|---|---|---|---|---|---|---|---|
| | 5 | 6 | 7 | 8 | 9 | 4 | 5 |
| Cure time T10 (sec) | 30 | 30 | 29 | 29 | 30 | 31 | 30 |
| Cure time T90 (sec) | 55 | 57 | 52 | 53 | 60 | 56 | 74 |
| T90-T10 (sec) | 25 | 27 | 23 | 24 | 30 | 25 | 44 |
| Appearance or color | colorless | colorless | colorless | colorless | colorless | colorless | colorless |
| Compression set (%) | 10 | 12 | 10 | 11 | 14 | 46 | 10 |
| Appearance or color after the test | colorless | colorless | colorless | colorless | colorless | colorless | colorless |

[Chemical Formula 2]

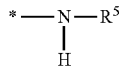

wherein $R^5$ is a $C_1$-$C_{15}$ monovalent hydrocarbon group or —$(CH_2)_p$—$Si(OR^6)_3$ wherein $R^6$ is a $C_1$-$C_4$ alkyl group or $SiR^7_3$ group (wherein $R^7$ is $C_1$-$C_4$ alkyl) and p is an integer of 1 to 6, and * designates a bonding site.

3. The silicone rubber composition of claim 1 or 2, further comprising (E) 1 to 100 parts by weight per 100 parts by weight of component (A) of a reinforcing filler.

4. The silicone rubber composition of claim 3 wherein component (E) is fumed silica having a specific surface area of at least 50 m²/g as measured by the BET method.

5. The silicone rubber composition of claim 1 wherein provided that T10 is a 10% cure time and T90 is a 90% cure time during measurement at 130° C. for 2 minutes, a value of T90-T10 is up to 40 seconds.

6. A cured silicone rubber which is formed by curing the silicone rubber composition of claim 1 and has a compression set of up to 30% after compressed 25% at 150° C. for 22 hours.

* * * * *